(12) United States Patent
Liang et al.

(10) Patent No.: US 8,795,678 B2
(45) Date of Patent: Aug. 5, 2014

(54) TLR-2 AGONISTS AND METHODS OF USE THEREOF

(75) Inventors: Shu-Mei Liang, Taipei (TW); Yu-Ching Chang, New Taipei (TW)

(73) Assignee: Academia Sinica, Taipei (TW)

( * ) Notice: Subject to any disclaimer, the term of this patent is extended or adjusted under 35 U.S.C. 154(b) by 141 days.

(21) Appl. No.: 13/470,554

(22) Filed: May 14, 2012

(65) Prior Publication Data

US 2012/0294878 A1    Nov. 22, 2012

Related U.S. Application Data

(60) Provisional application No. 61/485,806, filed on May 13, 2011.

(51) Int. Cl.
   *A61K 39/39*    (2006.01)
   *A61K 39/145*   (2006.01)
   *A61K 39/295*   (2006.01)

(52) U.S. Cl.
   USPC .................. 424/192.1; 424/209.1; 424/278.1

(58) Field of Classification Search
   None
   See application file for complete search history.

(56) References Cited

U.S. PATENT DOCUMENTS

| | | |
|---|---|---|
| 7,217,784 B2 | 5/2007 | Liang et al. |
| 7,323,546 B2 | 1/2008 | Liang et al. |
| 7,488,800 B2 | 2/2009 | Liang et al. |
| 7,604,961 B2 | 10/2009 | Liang et al. |
| 7,700,730 B2 | 4/2010 | Liang et al. |

FOREIGN PATENT DOCUMENTS

GB    2460283    * 11/2009    ............... C07K 1/18

OTHER PUBLICATIONS

Hedger et al (Trop. Anim. Hlth Prod. 18:21-25, 1986).*
Srinavasan et al (Veterinarski Arhiv 71 (1), 37-45, 2001).*
Cedillo-Barron et al (Journal of General Virology 82:1713-1724, 2001).*
Rossetti et al (Brazilian J. Med. Biol. Res. 26:591-603, 1993).*

* cited by examiner

*Primary Examiner* — Mary E Mosher
(74) *Attorney, Agent, or Firm* — Bozicevic, Field & Francis LLP; Pamela J. Sherwood

(57) ABSTRACT

Two new TLR2 agonists, VP1 and VP3, which are structural proteins of FMDV. Residues of VP3 responsible for TLR2 activation are identified. In vivo experiments showed that VP3-4xM2e is active as a vaccine adjuvant.

4 Claims, 7 Drawing Sheets

| group | MN titers | | |
|---|---|---|---|
| | California | NIBRG-14 | PR8 |
| PBS | 0 | 0 | 0 |
| HA + Alum | 8 | 16 | 8 |
| HA + VP3-4xM2e | 256 | 128 | 32 |

(B)

(C)

(D)

TLR-2 AGONISTS AND METHODS OF USE THEREOF

BACKGROUND OF THE INVENTION

Foot-and-mouth disease virus (FMDV) belongs to the Aphthovirus genus as a member of the Picornaviridae family. FMDV non-enveloped capsid is icosahedral symmetry, which is the classic structural characteristic of the picornavirus family. FMDV capsid composes of 4 structural proteins, VP1, VP2, VP3 and VP4, in which VP1, VP2 and VP3 are surface oriented, whereas VP4 is internal. FMDV elicits acute humoral antibody responses in infected or vaccinated animals, which have been considered to be the most important protective factor against FMD infection. There are increasing numbers of studies discussing about innate immune responses during FMDV infection or vaccination in recent years. FMDV is able to interact with and be internalized by porcine monocyte-derived dendritic cells in a heparin sulfate binding dependent manner. In addition, macrophage phagocytosis of FMDV occurs. Many kinds of pro-inflammatory cytokines and chemokines, such as IL-6, IL-8 and IL-12, are detected in pigs after high potency inactivated FMDV vaccination, suggesting that inactivated FMDV induces monocytic activities.

Toll-like receptors (TLRs) are pattern recognition receptors (PRRs) that recognize microbial components and endogenous ligands. Until now, 13 TLRs have been described in mice and 11 in human. When binding to specific ligands, TLRs initiate rapid intracellular signaling pathways involving activation of transcription factor NFκB, MAP kinases and interferon regulatory factors, which result in innate immune activation, including production of pro-inflammatory cytokines, chemokines, interferons and immunoglobulins and co-stimulatory molecules.

Among TLRs, TLR2 recognizes the broadest range of microbial derived agonists, including lipopolysaccharides from different bacterial strains, lipopeptides, lipoarabinomannans, lipomannans, glycosylphosphatidylinositol, lipoteichoic acid, various proteins including lipoproteins and glycoproteins, zymosan and peptidoglycan. TLR2 is also known to involve in virus or viral proteins induced signaling pathway and cytokine production, including Epstein-Barr virus, measles virus, Varicella-Zoster virus, hepatitis B and C virus, human and murine cytomegalovirus, herpes simplex virus, vaccinia virus and lymphocytic choriomeningitis virus. TLR2 can form a heterodimer with either TLR1 or TLR6, and recognizes different ligands by this way. For examples, triacyl lipopeptides and lipoarabinomannan can be recognized by TLR1/2, on the other hand, diacyl lipopeptides, zymosan and lipoteichoic acid can be recognized by TLR2/6. These expansions of ligand specificity cause a broad range of microbial recognition.

The signal transduction pathway mediated by the interaction between a ligand and a TLR is shared among most members of the TLR family and involves a toll/IL-1 receptor (TIR domain), the myeloid differentiation marker 88 (MyD88), IL-1R-associated kinase (IRAK), interferon regulating factor (IRF), TNF-receptor-associated factor (TRAF), TGFβ-activated kinase1, IκB kinases, IκB, and NF-κB. More specifically, for TLRs 1, 2, 4, 5, 6, 7, 8, 9 and 11, this signaling cascade begins with a PAMP ligand interacting with and activating the membrane-bound TLR, which exists as a homo-dimer in the endosomal membrane or the cell surface. Following activation, the receptor undergoes a conformational change to allow recruitment of the TIR domain containing protein MyD88, which is an adapter protein that is common to all TLR signaling pathways except TLR3. MyD88 recruits IRAK4, which phosphorylates and activates IRAK1. The activated IRAK1 binds with TRAF6, which catalyzes the addition of polyubiquitin onto TRAF6. The addition of ubiquitin activates the TAK/TAB complex, which in turn phosphorylates IRFs, resulting in NF-κB release and transport to the nucleus. NF-κB in the nucleus induces the expression of proinflammatory genes.

As a result of their involvement in regulating an inflammatory response, TLRs have been shown to play a role in the pathogenesis of many diseases, including autoimmunity, infectious disease and inflammation. Compositions for modulation of TLR activity are of interest for a variety of purposes, including use as an adjuvant. The present invention addresses this issue.

SUMMARY OF THE INVENTION

Compositions and methods for activation of TLR2 are provided. The capsid proteins VP1 and VP3 of Foot-and-mouth disease virus (FMDV) are identified herein as activators of mammalian TLR2. As agonists of TLR2, the VP1 and VP3 polypeptides induced bone marrow-derived dendritic cells maturation and cytokine production.

In some embodiments of the invention, a polypeptide fragment is provided, comprising or consisting of residues 91-150 of VP3, which fragment can be utilized for TLR2 activation. In some embodiments, a fusion protein of an antigen of interest with VP1, VP3 or an active fragment there, e.g. residues 91-150, residues 91-111, residues 1-150, etc. of VP3. In some embodiments the antigen of interest is an influenza virus protein, e.g. a matrix protein.

In some embodiments of the invention, the polypeptides of the invention are provided in a formulation suitable for use as an adjuvant. The polypeptides may be formulated with a vaccine antigen, e.g. co-formulated in a suspension or solution, fused to a polypeptide antigen of interest, and the like. For example, it is shown that VP3 fused to an influenza matrix protein is effective as an adjuvant against influenza virus.

In other embodiments, methods are provided for enhancing the immune response to an antigen of interest, the method comprising immunizing an individual mammal with formulation comprising the antigen of interest, a VP1, VP3 protein or active fragment thereof, in a pharmaceutically acceptable excipient.

BRIEF DESCRIPTION OF THE DRAWINGS

FIG. 1. I-FMDV activates TLR2 but not other TLRs. The HEK293T cells were transient transfected with p5xNF-kB-luc, EGFP-N1 (for normalization) and either a plasmid expressing different TLRs or pcDNA3.1 (empty vector) as indicated. Twenty four hours after transfection, the cells were treated with or without 90 μg/ml I-FMDV for 6 h. The cells were subsequently lysed and assayed for NF-kB activation. Data represent the mean±SD of triplicate from one of at least two independent experiments.

FIG. 2. I-FMDV activates TLR2. (A) The HEK-TLR2 cells were treated with 10 μg/ml TLR2 antibody, 10 μg/ml isotype control IgG or left untreated for 1 h, followed by 90 μg/ml I-FMDV treatment. NF-kB (upper panel) activation and IL-8 production (bottom panel) of HEK-TLR2 cells after 6 h treatment were measured by using reporter gene assay and ELISA, respectively. (B) Peritoneal macrophages were isolated from wild type or TLR2$^{-/-}$ mice and treated with I-FMDV at indicated concentration for 24 h. IL-6 productions in culture medium were measured by using ELISA. Data represent the mean±SD of triplicate from one of at least two independent experiments.

DETAILED DESCRIPTION OF THE EMBODIMENTS

Figure 3:
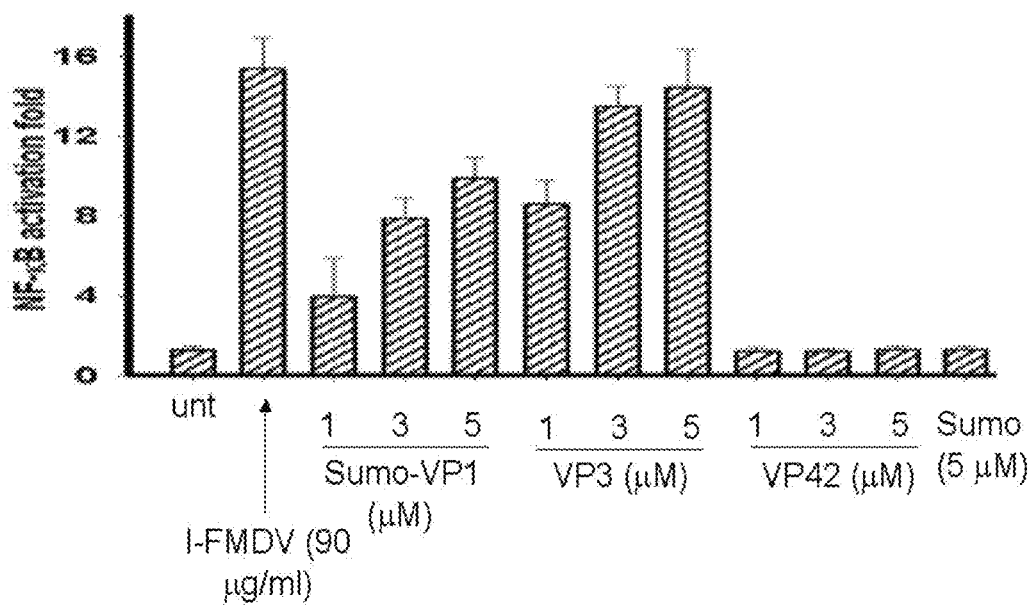
FIG. 3. VP3 activated NF-κB via TLR2. The HEK-TLR2 cells were transfected with p5xNF-κB-luc, EGFP-N1. Twenty-four hours after transfection, the cells were treated with or without different doses of I-FMDV, VP3, VP42, Sumo-VP1, or Sumo protein. NF-κB activation of the cells was measured by using reporter gene assay after 6 hours treatment. Data represent the mean±SD of triplicate from one of at least two independent experiments. (unt=untreated cells).

The present disclosure relates to compositions and methods of modulating inflammatory and immune responses through binding of agonist polypeptides to TLR2 in a subject mammal (e.g., human, non-human primate, rodent, etc.). In the studies described herein, it is shown that VP1 and VP3 are agonists of TLR2, and can provide for an adjuvant activity in immune stimulation.

In one embodiment of the present disclosure, a method includes providing a composition including a TLR2 agonist comprising or consisting of a VP1 or VP3 polypeptide, or an active fragment thereof, or a nucleic acid encoding a TLR2 agonist VP1 or VP3 polypeptide, or an active fragment thereof, and administering the composition to a subject. Administering the composition to the subject stimulates an immune response in the subject. The composition can include a TLR2 agonist VP1 or VP3 polypeptide, which when administered to a subject results in expression of at least one cytokine in a targeted cell or tissue. Administering the composition to the subject (e.g., human, non-human primate, rodent, etc.) can stimulate an immune response in the subject. The composition can be an adjuvant and administered to a subject (e.g., human, non-human primate, rodent) in combination with an antigen. The composition can further include a pharmaceutically acceptable carrier.

Before the present compositions and methods are described in further detail, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

The term "TLR2 agonist" as used herein refers to an agent that activates cell signaling through a TLR2. An agonist can be a naturally occurring activator of TLR2 or an agonist can be a non-naturally occurring activator of TLR2. Included as agonists are polypeptides identified herein, specifically the capsid proteins VP1 and VP3, and including without limitation a polypeptide comprising amino acid residues 91-150 of FMDV VP3. Such a polypeptide may consist or consist essentially of residues 91-150; residues 91-111; residues 1-150; etc. of FMDV VP3, or such a polypeptide may comprise residues 91-150, residues 91-111, residues 1-150, etc. of VP3 fused to a native or non-native sequence. For example, residues 91-150, residues 91-111, residues 1-150, etc. of VP3 of FMDV VP3 may be provided in the context of a VP3 protein, or may be fused to an antigenic polypeptide, to a cytokine, or other adjuvant sequence, and the like.

As used herein, the term "antagonist" means an agent that inhibits the effect of an agonist. For example, a TLR2 antagonist inhibits VP1 or VP3 polypeptide activation of TLR2. An antagonist can be a small molecule, a macromolecule (e.g., antibody), a peptide, and a nonpeptide. A small molecule, macromolecule (e.g., antibody), peptide, and nonpeptide can be naturally occurring or synthetic.

By the term "effective amount" is meant an amount of a composition as described herein that when administered to a subject, is sufficient for therapeutic efficacy (e.g. enhancing an inflammatory response).

As used herein, "immunologically effective amount," means that the administration of that amount to a subject, either in a single dose or as part of a series, is effective for treatment, e.g., stimulating an innate or adaptive immune response in a subject.

By the term "gene" is meant a nucleic acid molecule that codes for a particular protein, or in certain cases, a functional or structural RNA molecule. For example, the VP3 gene encodes the VP3 protein. VP3 nucleic acids (e.g., genes) are known in the art.

As used herein, a "nucleic acid," or "nucleic acid molecule," mean a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs. The term includes, e.g., a recombinant nucleic acid molecule incorporated into a vector, a plasmid, a virus, or a genome of a prokaryote or eukaryote.

As used herein, "polypeptide" is used to mean any peptide-linked chain of amino acids, regardless of length or post-translational modification, e.g., glycoslylation or phosphorylation. By the term "VP3 polypeptides" is meant a protein, or a fragment thereof, corresponding to the VP3 capsid protein of FMDV. Similarly, "VP1" refers to the VP1 capsid protein of FMDV.

The amino acid sequence of VP3 is set forth in SEQ ID NO:1 GIFPVACSDG YGGLVTTDPK TADPVYGKVF NPPRNLLPGR FTNLLDVAEA CPTFLHFDGD VPYVTT-KTDS DRVLAQFDLS LAAKHMSNTF LAGLAQYYTQ YSGTINLHFM FTGPTDAKAR YMVAYAPPGM EPPKT-PEAAA HCIHAEWDTG LNSKFTFSIP YLSAADYAYT ASDVAETTNV QGWVCLFQIT HGKADGDALV VLA-SAGKDFD LRLPVDARTQ A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

By the phrase "expression control sequence" is meant a nucleic acid that regulates the replication, transcription and translation of a coding sequence in a recipient cell. Examples of expression control sequences include promoter sequences, polyadenylation (pA) signals, introns, transcription termination sequences, enhancers, upstream regulatory domains, origins of replication, and internal ribosome entry sites. The term "promoter" is used herein to refer to a DNA regulatory sequence to which RNA polymerase binds, initiating transcription of a downstream (3' direction) coding sequence.

Methods described herein include a composition including an agent (e.g., VP3 TLR2 agonist polypeptide or a nucleic acid encoding VP3 polypeptide) that when administered to a subject, activates TLR2 and stimulates an immune response in the subject. Such an agent can activate TLR2 by, for example, interacting with TLR2 (e.g., VP3 polypeptide binding to TLR2). An agent that activates TLR2 can alter transcription of genes, increase translation of mRNA or increase the activity of proteins that are involved in mediating TLR2 cellular processes. For example, an agent that activates TLR2 can induce expression of IL-8, IL-12p40, and IL-23.

A composition including an agent that activates TLR2 (e.g., a VP3 polypeptide, a mimetic of VP3 polypeptide, etc.) can be administered to a subject (e.g., rodent, human, non-human primate) for stimulating an immune response in a subject in need thereof (e.g., a subject suspected of having exposure to infectious disease, a subject having cancer, etc.).

Administration of a composition including an agent that activates TLR2 to a subject can induce expression of immunomodulatory cytokines such as IL-12p40, IL-8, and IL-23. In some embodiments, a composition including an agent that activates TLR2 is an adjuvant and is administered with a specific antigen to potentiate the effect of vaccination against an infectious agent or abnormal cell such as a cancer cell. Such a composition includes an immunologically effective amount of the agent that activates TLR2.

The compositions described herein can be administered to subjects including human beings in any suitable formulation by any suitable method. For example, compositions including an agent that activates TLR2 (e.g., VP3 polypeptide or a nucleic acid encoding VP3 polypeptide) may be directly introduced into a subject, including by intravenous (IV) injection, intraperitoneal (IP) injection, or in situ injection into target tissue. To improve patient compliance, a drug may be made orally effective. When used as a vaccine adjuvant, it will go with the vaccination method or route. For example, a conventional syringe and needle can be used to inject a composition including an agent that modulates TLR2 activation into a subject. Parenteral administration by injection can be performed, for example, by bolus injection or continuous infusion. Formulations of injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, compositions may be in powder form (e.g., lyophilized) for constitution with a suitable vehicle, for example, sterile pyrogen-free water, before use.

The compositions of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16.sup.th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

In some embodiments, a composition including an immunologically effective amount of agent that activates TLR2 is administered to a subject to stimulate an immune response in the subject. An immunologically effective amount varies depending upon the health and physical condition of the subject to be treated, the taxonomic group of individual to be treated (e.g. human, nonhuman primate, etc.), the capacity of the subject's immune system to synthesize antibodies, the degree of protection desired, the formulation of the vaccine, the treating doctor's assessment of the medical situation, the condition to be treated or prevented, and other relevant factors. It is expected that the amount will fall in a relatively broad range that can be determined through routine trials.

EXAMPLES

Capsid Protein VP3 is a TLR2 Agonist

The identification of different Toll-like receptors (TLRs) and their associated ligand, together with cytokine production and dendritic cell maturation following TLR engagement have facilitated vaccine research and formulation. In this study, capsid protein VP3 of foot- and mouth disease virus activated TLR2. Residues 91-150; residues 91-111; residues 1-150 of VP3 were determined to be important for TLR2 activation, using different VP3 deletion mutants. VP3 induced maturation and cytokine production of bone marrow-derived dendritic cells. Furthermore, VP3 fused with four tandem copies of ectodomain of the conserved influenza matrix protein M2 (VP3-4xM2e) was effective as an adjuvant against influenza virus in a mouse challenge model. VP3-4xM2e also provides cross protection against lethal challenge with influenza A viruses including the California/07/2009 (H5N1), NIBRG-14 (H5N1), and PR8 (H1N1) influenza viruses. Taken together; these findings indicated that VP3 is a novel TLR2 agonist, with utility has an adjuvant.

In this study, it was found that the I-FMDV induces NF-κB activation via TLR2. The FMDV structural proteins, VP1 and VP3, were identified as TLR2 agonists. The further analysis proved that the residues 91-150 of VP3 are important for TLR2 activation. The potential ability of VP3 as a vaccine adjuvant was also evaluated in this study.

Material and Methods

Reagents. Pam3CSK4 were purchased from Invivogen (CA, USA). Mouse monoclonal anti-mouse/human TLR2 and mouse monoclonal anti-mouse CD14 antibody for functional blocking assay were purchased from eBioscience (CA, USA), mouse isotype control IgG was purchased from PIERCE (IL, USA). The chlorpromazine (CPZ) or genistein were purchased from Sigma-Aldrich (St. Louis, Mo.).

BEI-inactivated FMDV (1-FMDV) preparation. FMDV strain O/TWN/97 was used and grown in BHK-21 cells. Forty hours post-infection samples were collected and clarified by centrifugation at 4,000 rpm. BEI was prepared by adding 0.1 M of bromoethylamine hydrobromide to a cooled solution of 0.2 N sodium hydroxide and left at room temperature for cyclization. BEI was added to clarified virus culture at final concentration of 1 mM and incubated at 37° C. with continuous stirring for 24 hours. Viral capsid particles after BEI inactivated treatment were collected by sucrose gradient centrifugation and quantified by measuring protein concentration by Bradford assay (PIERCE, IL, USA).

Cell culture. Human embryonic kidney HEK-293T cells and mouse RAW264.7 macrophages were obtained from the American Type Culture Collection (VA, USA) and cultured in Dulbecco's modified Eagle's medium supplemented with 10% heat-inactivated fetal bovine serum, 50 μg/ml penicillin, 50 μg/ml streptomycin sulfate and 100 μg/ml neomycin sulfate (Invitrogen, CA, USA). All cells were cultured in a humidified atmosphere of 5% $CO_2$ at 37° C. TLR2-expressing HEK293 stable cell line 293-HA-TLR2 (HEK-TLR2) were kindly provided by Dr. Konon Peck (The Institute of Biomedical Sciences, Academia Sinica, Taipei, Taiwan) and cultured in the same media as HEK-293T except adding 10 μg/ml blasticidin (Invivogen, Calif., USA).

Peritoneal macrophage isolation. The wild type C57BL/6 mice were purchased from the National laboratory animal center (Taipei, Taiwan). $TLR2^{-/-}$ mice were purchased from The Jackson Lab (Maine, USA). Macrophages were isolated from peritoneal exudates of mice 3 days after intraperitoneal injection of 2 ml of 3% wt/vol thioglycolate solution. The isolated macrophages were cultured in RPMI-1640 medium plus 10% heat-inactivated fetal bovine serum, 50 μg/ml penicillin, 50 μg/ml streptomycin sulfate and 100 μg/ml neomycin sulfate (Invitrogen, CA, USA).

NF-κB reporter gene assay. HEK293T cells ($1.5 \times 10^4$ cells/well) were seeded onto 96-well plate and cultured overnight. The cells were transfected using Lipofectamine-2000 (Invitrogen, CA, USA) plus 0.05 μg of TLR-expressing plasmid, 0.03 μg of p5xNFκB-luc plasmid (Stratagene, Tex., USA) and 0.02 μg of EGFP-N1 (Clontech, Palo Alto, Calif., USA) for 24 h according to manufacturer's instruction. The cells were incubated with TLR ligands for 6 h, washed twice with PBS then lysed. NFκB luciferase activities were measured using the luciferase assay system (Promega, Wis., USA) according to the manufacturer's instruction. Levels of firefly luciferase expression were normalized by the intensity of EGFP as a control for transfection efficiency and expressed as fold stimulation over unstimulated pcDNA3.1 empty vector control.

ELISA. RAW264.7 cells ($8 \times 10^4$ cells/well) were seeded onto 24-well plate and cultured overnight. The cells were treated with stimulants for 24 hours. Cytokine productions in culture medium were measured by using ELISA assay kits (Invitrogen, CA, USA) according to manufacturer's instructions.

Recombinant protein production. An improved SUMO fusion protein expression system was carried out to produce the water-soluble recombinant Sumo-VP1, VP3, different VP3 deletion mutants, or VP42 protein as described previously (Lee et al, 2009). The *E. coli* produced recombinant proteins were first purified by cobalt beads and then subjected to proteolytic digestion with a home-made SUMO protease, $His_6$-$Ulp1_{403-621}$-$His_6$. The SUMO-fusion tag was removed by cobalt beads. Finally, the recombinant VP3 or VP42 proteins was obtained in the supernatant Dendritic cell isolation. For isolation of dendritic cells, whole bone marrow was isolated from the leg bones of wild type C57BL/6 and $TLR2^{-/-}$ mice, and cells were grown in complete RPMI1640 containing recombinant murine GM-CSF (10 ng/mL). On day two and day four, the fresh medium with GM-CSF was added. On day six of the culture, immature DCs were collected and replated in 6 well plate. The DCs were treated with 1 μM VP3 or 1 μg/ml Pam3Csk4 for 48 h. To determine the maturation of DCs, the flow cytometric analysis of the expression of BMDCs surface markers (CD80 and CD86) was applied.

Flow cytometric analysis of the expression of BMDCs surface markers. BMDCs were incubated in the absence (sham-treated) or presence of 1 μM VP3 or 1 μg/ml Pam3Csk4 for 48 h. The treated BMDCs were immunostained with CD86-PE, CD80-FITC, and their isotype control antibodies for 30 min on ice. After PBS wash, the samples were analyzed by flow cytometer. The position of quadrants was determined by BMDCs stained with FITC- and PE-conjugated isotype-matched control antibodies. The numbers at upper right of corner indicated the percentage of matured DC.

Peptide synthesis. The peptides representing the residues 140-149 or 131-149 of VP3 were synthesized by Institute Biological Chemistry research facilities of Academica Sinica.

Microneutralization titers measurement. The sera obtained from immunized mice at week 4 before virus challenge were inactivated by incubation at 56° C. for 1 h. The freshly prepared California/07/2009(H5N1), NIBRG-14 (H5N1), and PR8 (H1N1) virus (National Institute for Biological Standards and Control, Potters Bar, U.K.) was quantified with the median tissue culture infectious dose (TCID50). The 100-fold TCID50 of virus was mixed in equal volume with 2-fold serial dilutions of inactivated serum stock solution in 96-well plates and incubated for 1 h at 37° C. The mixture was added onto the MDCK cells ($1.5 \times 10^4$ cells per well) on the plates, followed by incubation at 37° C. for 3 days. The cells were washed with ice-cold 1×PBS, fixed in methanol solution, and added 200 μl 0.5% crystal violet. After three times wash by ddH2O, the plates were air dry for o/n. If a serum sample contains antibodies that block viral infection, most of the cells will survive and present violet color; if the virus can't be blocked by the serum, cells will be infected, round up and detach from the cell culture plate, thus no violet staining is visible for infected cells. The MN titers are expressed as the highest dilution at which virus infection is blocked.

Vaccination and Challenge. Male 6- to 8-week-old BALB/c mice (n=6) were immunized intramuscularly with 5 μg of HA protein in combination with 50 μg of Aluminum hydroxide (Alum; Sigma), 30 μg of VP3-4xM2e, or control PBS at week 0 and 2. The immunized mice were intranasally challenged with a lethal dose of California/07/2009(H5N1), NIBRG-14 (H5N1), and PR8 (H1N1) virus at week 4. The survival number of mice were monitored daily for 14 days after the challenge. The animal experiments were evaluated and approved by the Institutional Animal Care and Use Committee of Academia Sinica.

Results

Figure 1:
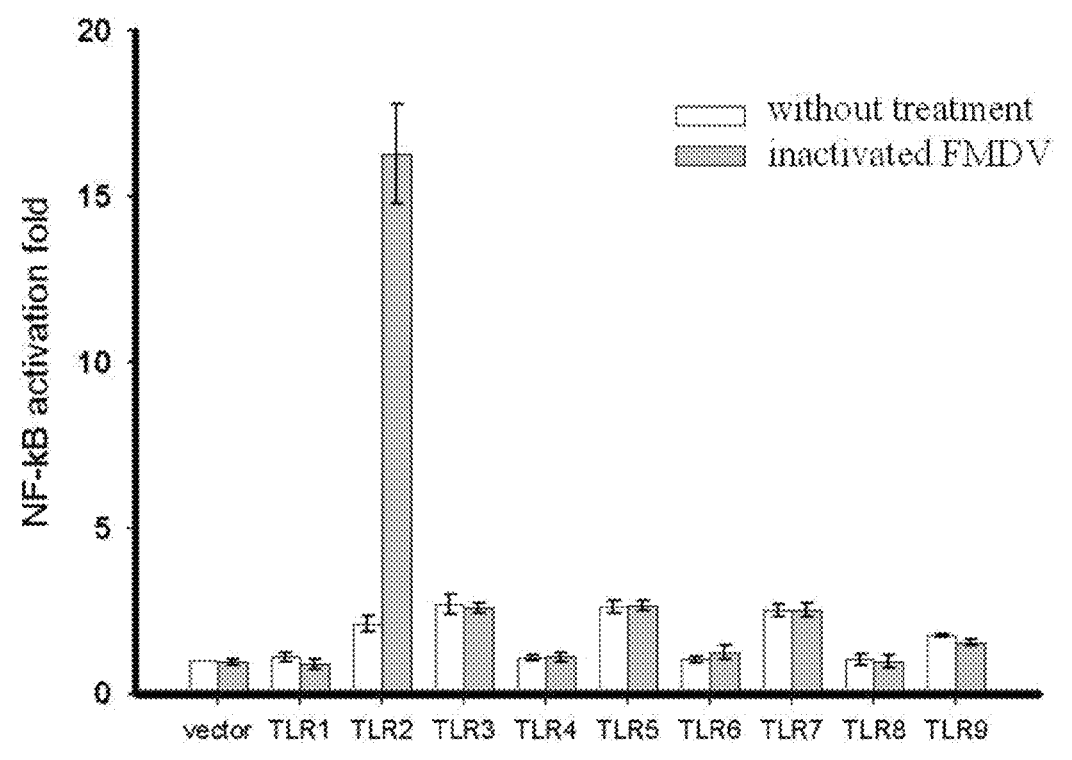
Figure 2:
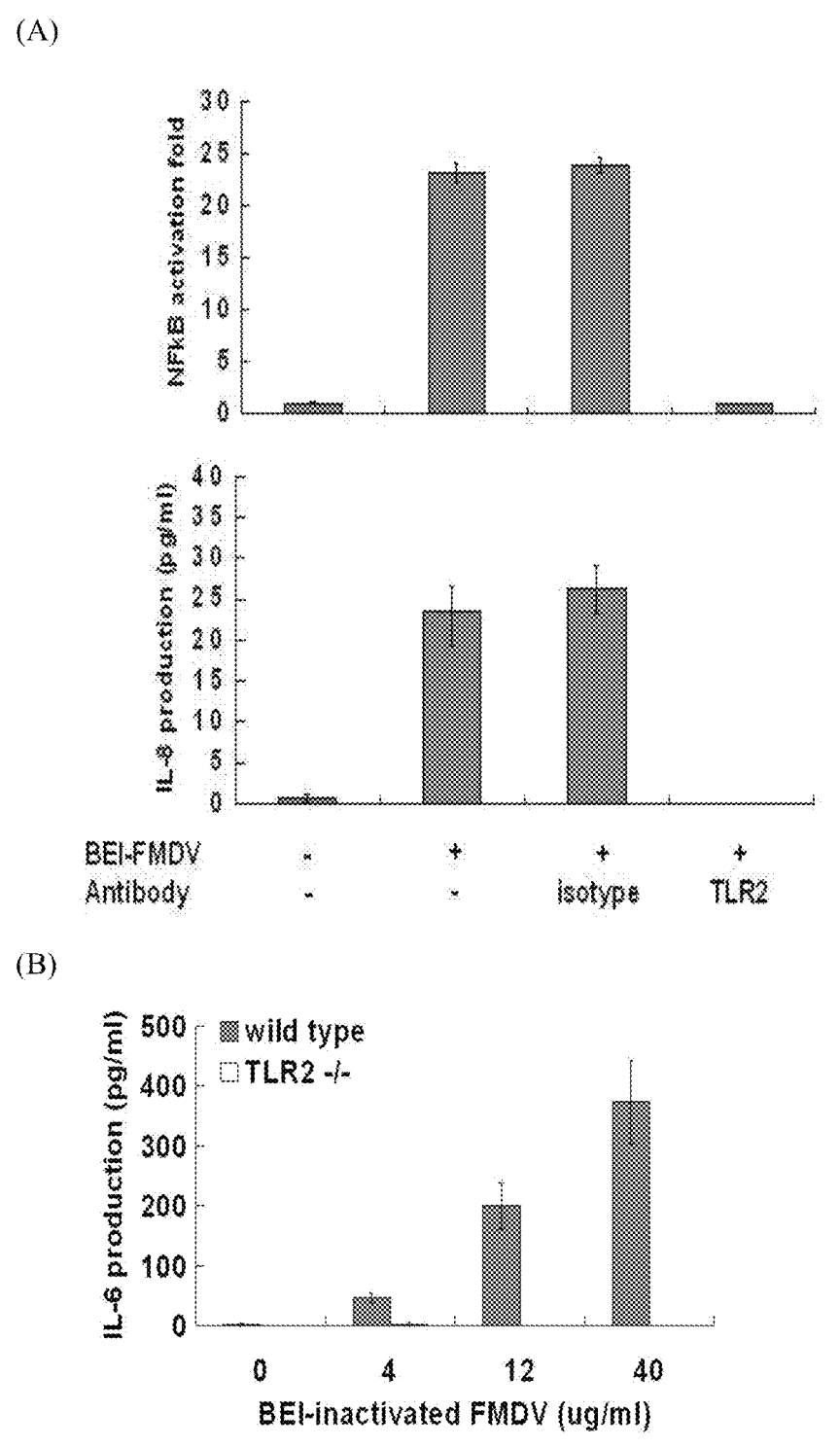

I-FMDV activates TLR2. Innate immune recognition is mediated by pattern recognition receptors (PRRs) to detect microbial substances and further activates immune responses. Among several kinds of PRRs, Toll-like receptors (TLRs) are best characterized (Medzhitov, 2007). We examined whether TLRs could recognize I-FMDV to activate immune cells. The TLRs-lacking HEK293T cells were transiently transfected with specific TLRs-expressing and NF-κB reporter plasmid to evaluate if I-FMDV could activate NF-κB via TLR. We found that I-FMDV induced NF-κB activation through TLR2, but not through other TLRs (FIG. 1). To further confirm that TLR2 is a receptor for I-FMDV, TLR2 specific antibody was used to block the extracellular domain of TLR2 on cell membrane of TLR2-stable expressing HEK293T (HEK-TLR2) cells prior to addition of 1-FMDV. NF-κB activation or IL-8 production induced by I-FMDV were significantly decreased when cells were pretreated with TLR2 specific antibody, but not with isotype control IgG (FIG. 2A). These results show that NF-κB activation or proinflammatory production induced by I-FMDV could be blocked by anti-TLR2 antibody.

We further investigated the cytokine production in peritoneal macrophages isolated from wild type or TLR2$^{-/-}$ mice that treated with I-FMDV (FIG. 2B). Peritoneal macrophages isolated from TLR2$^{-/-}$ mice did not respond to I-FMDV stimulation (FIG. 2B). These data indicated that I-FMDV induced cytokine production in macrophages through TLR2. Overall, these results suggest that TLR2 but not other TLRs is the specific receptor for I-FMDV.

VP3 activate TLR2. The FMDV capsid composes of four structural proteins which are VP1, VP2, VP3 and VP4. In our previous study, we have found that recombinant VP1 protein could activate TLR2 (Liang (2010) Process to produce fibrillar proteins and method of treatment using fibrillar proteins (854). England Patent GB2460283). To test the activity of other FMDV capsid proteins in activation of TLR2; we produced the recombinant VP1, VP3 and VP42 protein from *E. coli*. In this study, the SUMO fusion technology was used to obtain the soluble capsid subunit (Lee et al. (2009) Production of FMDV virus-like particles by a SUMO fusion protein approach in *Escherichia coli. J Biomed Sci* 16: 69). The recombinant VP1 with SUMO tag (Sumo-VP1) was used in this experiment instead of SUMO-tag free VP1 because the removal of Sumo-tag cause the protein precipitation. The NF-κB activation was assessed in HEK-TLR2 cells in response to sumo-VP1, VP3 or VP42. FIG. 3 showed that in addition to Sumo-VP1, VP3 also activated TLR2 in a dose dependent manner. In contrast with VP1 and VP3, the VP42 or SUMO protein could not activate NF-κB even though the high concentration of VP42 or SUMO was used. The result demonstrates that VP1 and VP3 are the components for FMDV to activate TLR2 in cells.

Figure 4:
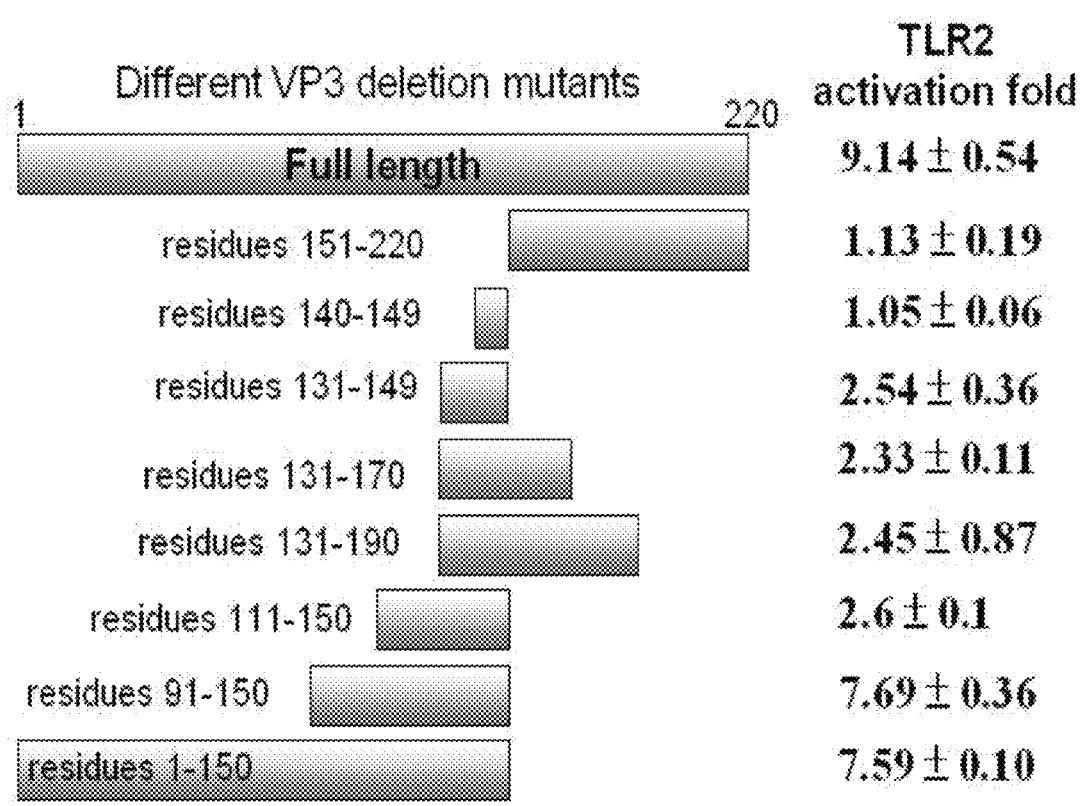
FIG. 4. The central region of VP3 is responsible for TLR2 activation. The HEK-TLR2 cells were transfected with p5xNF-κB-luc, EGFP-N1. Twenty-four hours after transfection, the cells were treated with different VP3 deletion mutants. NF-κB activation of the cells was measured by using reporter gene assay after 6 h treatment. Data represent the mean±SD of triplicate from one of at least two independent experiments. (unt=untreated cells).

The residues 91-150 of VP3 are responsible for TLR2 signaling. To look for the important region of VP3 for TLR2 activation, different VP3-deletion mutants were expressed with Sumo-tag from *E. coli*. Only two peptides representing the residues 140-149 or 131-149 of VP3 were chemical synthesized because the molecular weight too small to be purified. The NF-κB activation was assessed in HEK-TLR2 cells in response to different VP3-deletion proteins. Although the short peptide consisting of residues 131-149 of VP3 was enough to activate TLR2, the activation folds was well below the full length VP3. The VP3 fragment protein consisting of residues 91-150, which contain the residues 131-149 of VP3 with additional amino acids, induced TLR2 activation as well as full length VP3 (FIG. 4). The result show that the residues 91-150 of VP3 are responsible for TLR2 activation.

Figure 5:
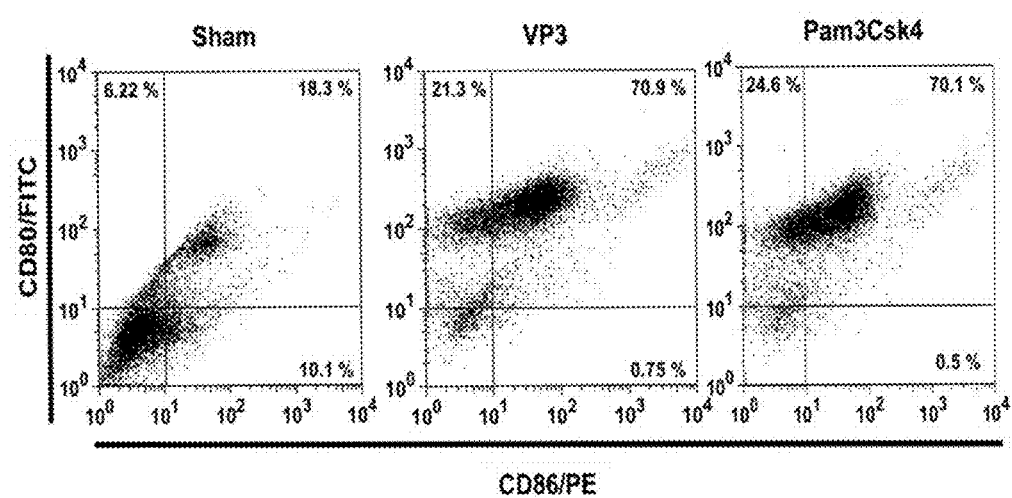
FIG. 5. VP3 induces maturation of bone marrow-derived dendritic cells (BMDCs). Flow cytometric analysis of the expression of BMDCs surface markers (CD80 and CD86). BMDCs were incubated in the absence (sham-treated) or presence of 1 μM VP3 or 1 μg/ml Pam3Csk4 for 48 h before immunostaining and flow cytometric analysis. The position of quadrants was determined by BMDCs stained with FITC- and PE-conjugated isotype-matched control antibodies. The numbers at upper right of corner indicated the percentage of matured DC.
Figure 6:
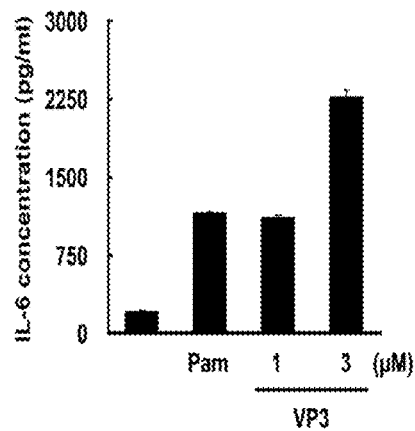
FIG. 6. Production of cytokines by BMDCs in response to VP3. BMDCs were incubated in the absence or presence of 1 μg/ml Pam3Csk4 or VP3 at the specific concentration for 48 h before the supernatant was harvested for the measurement of (A) IL-6, (B) IL-12 and (C) TNF-α levels by ELISA assay.
Figure 6:
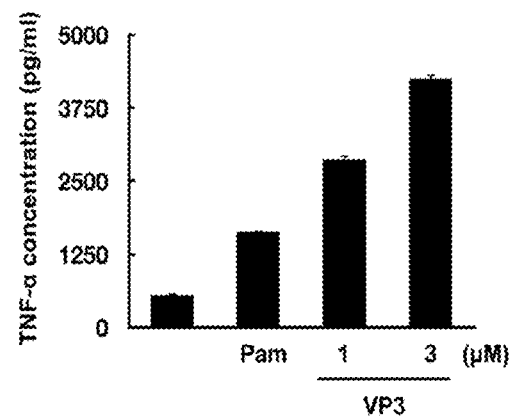
Figure 6:
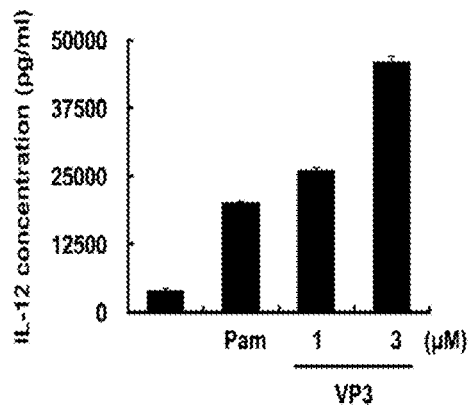
Figure 7:
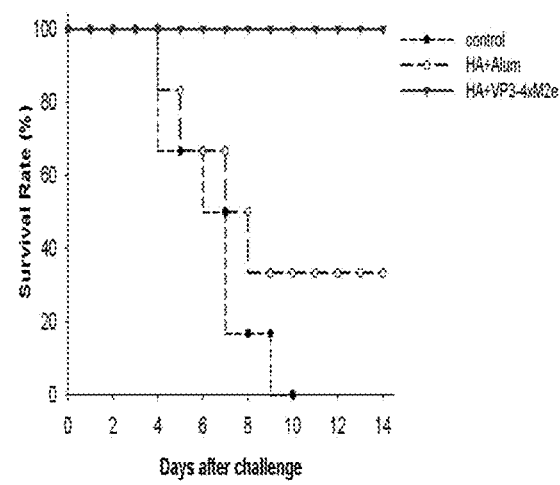
FIG. 7. Adjuvant effect of VP3-4xM2e.BALB/c mice (n=6) were immunized intramuscularly with 5 μg of HA protein in combination with 50 μg of aluminum hydroxide (Alum), 30 μg of VP3-4xM2e, or control PBS at week 0 and 2. (A) The sera obtained from immunized mice at week 4 were used for microneutralization (MN) titers measurement. To evaluate the protective effect of vaccine, the immunized mice were intranasally challenged with a lethal dose of (B) California/07/2009(H5N1), (C) NIBRG-14 (H5N1), and (D) PR8 (H1N1) influenzavirus at week 4. The survival rate of mice were monitored daily for 14 days after the challenge.
Figure 7:
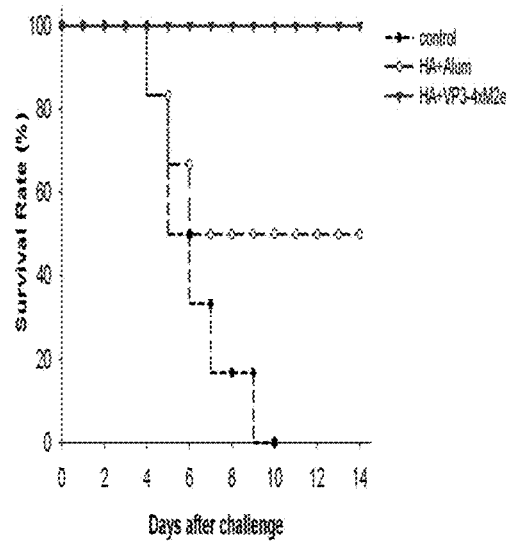
Figure 7:
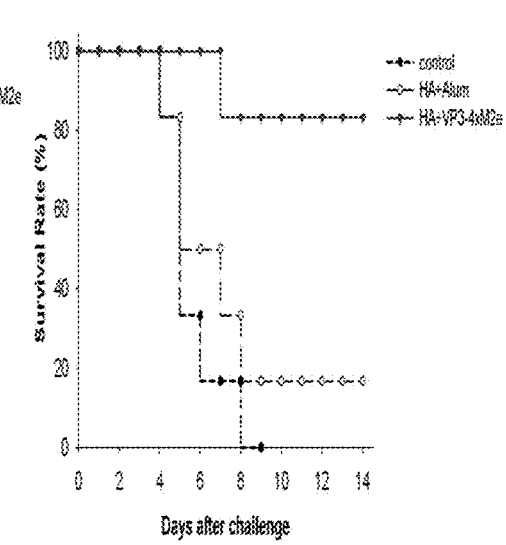

VP3 could be a candidate of vaccine adjuvant. TLR agonists are being developed as adjuvants to prevent cancer and infectious disease (Kanzler et al. (2007)*Nat Med* 13(5): 552-559). We next studied the role of VP3 in immune cells and explored the potential capacity of using VP3 as a vaccine adjuvant. Because TLR on dendritic cell (DC) are important adjuvant receptors and support the molecular basis of adjuvant activity (Takeda et al, 2003), we examined the maturation or cytokine production in DC upon VP3 treatment. The results showed that VP3 induced bone marrow-derived dendritic cells (BMDC) maturation (FIG. 5) and cytokine production (FIG. 6). To further examine the possibility of VP3 as a vaccine adjuvant, the recombinant VP3 protein was fused with four tandem copies of ectodomain of the conserved influenza matrix protein M2 (VP3-4xM2e) and co-immunized with hemagglutinin antigen (HA). Mice immunized with HA in the presence of VP3-4xM2e showed the higher microneutralization (MN) titers and protective effect than Aluminum hydroxide (Alum), a common vaccine adjuvant, in a challenge study (FIG. 7). In addition, we also found that VP3-4xM2e provided cross protection against lethal challenge with different influenza sub-types virus including the California/07/2009(H5N1), NIBRG-14 (H5N1), and PR8 (H1N1) influenza viruses (FIG. 7). Taken together, these results demonstrate that VP3 is useful as a vaccine adjuvant.

CONCLUSION

Although many TLR2 ligands have been discovered and developed, the development of a safe and effective novel TLR2 agonist for vaccine adjuvant is an endless work. In this study, we identified two TLR2 agonists, VP1 and VP3, both of which are structural proteins of FMDV. The further study indicated that the residues 91-150; residues 91-111; residues 1-150 of VP3 are responsible for TLR2 activation. Furthermore, in vivo experiments also demonstrated that VP3-4xM2e enhances the protective effect of HA vaccine against different influenza sub-types virus. These findings indicated that VP1 and VP3 are novel TLR2 agonists.

What is claimed is:

1. A method of stimulating an immune response in a subject, the method comprising:
   administering to said subject a composition comprising one or more of:
   (a) a polypeptide consisting of Foot and Mouth Disease Virus (FMDV) VP3 residues 91-150 fused to an antigen;
   (b) a polypeptide consisting of FMDV VP3 residues 91-111 fused to an antigen;
   (c) a polypeptide consisting of FMDV VP3 residues 1-150 fused to an antigen;
   wherein administering the composition to the subject stimulates an immune response.

2. An adjuvant formulation, comprising:
   an effective dose of one or more of:
   (a) a polypeptide consisting of Foot and Mouth Disease Virus (FMDV) VP3 residues 91-150 fused to an antigen;
   (b) a polypeptide consisting of FMDV VP3 residues 91-111 fused to an antigen;
   (c) a polypeptide consisting of FMDV VP3 residues 1-150 fused to an antigen;
   a pharmaceutically acceptable excipient.

3. A method of stimulating an immune response to influenza viruses in a subject by giving TLR2 agonists as vaccine adjuvant to stimulate TLR2 and facilitate immune responses of the subject to influenza antigens, the method comprising:
   administering to said subject a composition comprising influenza antigens and one or more of:
   Foot and Mouth Disease Virus (FMDV) FMDV VP3 polypeptide;
   a nucleic acid encoding said VP3 polypeptide;
   a polypeptide consisting of FMDV VP3 residues 91-150 of FMDV VP3;
   a polypeptide consisting of FMDV VP3 residues 91-111 of FMDV VP3; and
   a polypeptide consisting of FMDV VP3 residues 1-110 of FMDV VP3.

4. The method of claim 3, wherein one or more the TLR2 agonists are fused to the antigen.

* * * * *

SEQUENCE LISTING

<160> NUMBER OF SEQ ID NOS: 1

<210> SEQ ID NO 1
<211> LENGTH: 220
<212> TYPE: PRT
<213> ORGANISM: Foot and Mouth Disease Virus

<400> SEQUENCE: 1

```
Gly Ile Phe Pro Val Ala Cys Ser Asp Gly Tyr Gly Gly Leu Val Thr
1               5                   10                  15

Thr Asp Pro Lys Thr Ala Asp Pro Val Tyr Gly Lys Val Phe Asn Pro
            20                  25                  30

Pro Arg Asn Leu Leu Pro Gly Arg Phe Thr Asn Leu Leu Asp Val Ala
            35                  40                  45

Glu Ala Cys Pro Thr Phe Leu His Phe Asp Gly Asp Val Pro Tyr Val
    50                  55                  60

Thr Thr Lys Thr Asp Ser Asp Arg Val Leu Ala Gln Phe Asp Leu Ser
65                  70                  75                  80

Leu Ala Ala Lys His Met Ser Asn Thr Phe Leu Ala Gly Leu Ala Gln
                85                  90                  95

Tyr Tyr Thr Gln Tyr Ser Gly Thr Ile Asn Leu His Phe Met Phe Thr
            100                 105                 110

Gly Pro Thr Asp Ala Lys Ala Arg Tyr Met Val Ala Tyr Ala Pro Pro
            115                 120                 125

Gly Met Glu Pro Pro Lys Thr Pro Glu Ala Ala Ala His Cys Ile His
        130                 135                 140

Ala Glu Trp Asp Thr Gly Leu Asn Ser Lys Phe Thr Phe Ser Ile Pro
145                 150                 155                 160

Tyr Leu Ser Ala Ala Asp Tyr Ala Tyr Thr Ala Ser Asp Val Ala Glu
                165                 170                 175

Thr Thr Asn Val Gln Gly Trp Val Cys Leu Phe Gln Ile Thr His Gly
            180                 185                 190

Lys Ala Asp Gly Asp Ala Leu Val Val Leu Ala Ser Ala Gly Lys Asp
            195                 200                 205

Phe Asp Leu Arg Leu Pro Val Asp Ala Arg Thr Gln
            210                 215                 220
```